United States Patent [19]

Eckwert et al.

[11] Patent Number: 4,647,678

[45] Date of Patent: Mar. 3, 1987

[54] PROCESS FOR THE EPOXIDATION OF OLEFINICALLY UNSATURATED HYDROCARBON COMPOUNDS WITH PERACETIC ACID

[75] Inventors: Klemens Eckwert, Duesseldorf; Lutz Jeromin, Hilden; Alfred Meffert, Monheim; Eberhard Peukert; Bernhard Gutsche, both of Hilden, all of Fed. Rep. of Germany

[73] Assignee: Henkel Kommanditgesellschaft auf Aktien, Duesseldorf, Fed. Rep. of Germany

[21] Appl. No.: 813,444

[22] Filed: Dec. 26, 1985

[30] Foreign Application Priority Data

Dec. 31, 1984 [DE] Fed. Rep. of Germany ....... 3447864

[51] Int. Cl.$^4$ ............................................ C07D 301/14
[52] U.S. Cl. ..................................... 549/528; 549/525
[58] Field of Search ................................ 549/525, 528

[56] References Cited

FOREIGN PATENT DOCUMENTS 3320219 12/1984 Fed. Rep. of Germany .

OTHER PUBLICATIONS

H. K. Latourette J. Am. Oil Chem. S. 37 1960, pp. 559–563.
H. K. Latourette J. Am. Oil Chem. S 34 1957, pp. 161–164.

Primary Examiner—Norma S. Milestone
Attorney, Agent, or Firm—Ernest G. Szoke; Henry E. Millson, Jr.; Mark A. Greenfield

[57] ABSTRACT

The epoxidation of terminally and/or internally olefinically unsaturated hydrocarbon compounds which are liquid at 50° to 100° C. and at atmospheric pressure (oil phase), in which the oil phase is treated with an acid phase containing acetic acid, hydrogen peroxide and peracetic acid in aqueous solution, after which the aqueous acid phase is separated from the oil phase, the peracetic acid in the aqueous acid phase is regenerated and the regenerated aqueous acid phase is returned to the epoxidation reactor. Epoxidation is carried out using an aqueous acid phase containing at most about 10% by weight of peracetic acid, and the peracetic acid content in the aqueous acid phase is reduced by at most about 50%, based on the peracetic acid content of the aqueous acid phase used, after a single passage through the epoxidation stage. After separation from the oil phase, the aqueous acid phase preferably is cooled before regeneration.

21 Claims, 3 Drawing Figures

PROCESS FOR THE EPOXIDATION OF OLEFINICALLY UNSATURATED HYDROCARBON COMPOUNDS WITH PERACETIC ACID

BACKGROUND OF THE INVENTION

1. Field of the Invention

This invention relates to a process for the epoxidation of olefinically unsaturated hydrocarbon compounds with peracetic acid formed by the catalytic reaction between hydrogen peroxide and acetic acid. The process of the present invention is particularly suitable for epoxidating terminally and/or internally olefinically unsaturated hydrocarbon compounds which are liquid under normal (atmospheric) pressure at a temperature within the range of about 50° to 100° C.

2. Description of Related Art

The epoxidation of unsaturated fatty acid derivatives, primarily soya oil, is carried out industrially on a large scale. The epoxidized product comprises a PVC compatible plasticizer. The product simultaneously acts as a heat stabilizer in PVC. Epoxidized soya oil also has been approved as an additive for plastics used with foods.

In current commerical practice, performic acid is still used as the epoxidizing agent. The performic acid is obtained in situ by reaction between formic acid and hydrogen peroxide. Even so, unsatisfactory yields of epoxide product generally are obtained with performic acid in epoxidation processes involving alpha-olefins and unsaturated fatty alcohols. Unfortunately, it is not possible, based on safety considerations, to overcome this problem simply by increasing the concentrations of hydrogen peroxide and formic acid in the reaction mixture.

The rate of formation of the corresponding peracid by reaction between acetic acid and hydrogen peroxide is comparatively slow. However, the velocity of the epoxidation reaction using peracetic acid as the epoxidizing agent appears higher than where performic acid is used. Another potential advantage of using peracetic acid for expoxidation relative to performic acid is the greater stability of peracetic acid. In fact, peracetic acid may be formed on an industrial scale outside the epoxidation reactor with greater safety and with fewer decomposition losses than can performic acid.

It also is known that acetic acid and hydrogen peroxide can be reacted to form peracetic acid in the presence of strongly acidic cation exchange resins, based for example on polystyrene. Particularly suitable catalyst resins are gel-like and/or macroporous resins containing sulfonic acid residues as ion exchange groups. In this connection, reference is made, for example, to H. K. Latourette et al., *J. Am. Oil Chem. S.:* 37 (1960), pages 559 to 563; to R. J. Gall et al., *J. Am. Oil Chem. S.:* 34 (1957), pages 161 to 164 and to the literature cited therein. Ion exchange resins marketed under the tradenames Amberlite IR-120 by Rohm & Haas Co.; Chempro C-20; Dowex 50X by the Dow Chemical Co. and other equivalent resins are mentioned in these references as suitable ion exchange resin catalysts.

In particular, it is taught that peracetic acid is formed in situ by passing the hydrocarbon starting material to be epoxidized together with hydrogen peroxide and acetic acid over the heterogeneous solid resin catalyst. Alternatively, the various reactants are agitated together with the resin catalyst in a stirred reactor. However, these methods of carrying out the epoxidation reaction have serious disadvantages in terms of industrial application. For example, the unsaturated hydrocarbon compound normally wets the catalyst surface, thus blocking its pores and resulting in rapid deactivation of the resin catalyst for the production of peracetic acid. In the stirred-reactor embodiment, the catalyst particles tend to be mechanically abraded thus accelerating the above-described effect.

Because the epoxidation reaction generally requires a temperature above about 50° C., for example up to about 80° C., the thermal load on the resin catalyst in these arrangements also is comparatively high. Finally, rapid swelling and, in some cases, even partial dissolution of the ion exchange resin catalyst is observed under the effect of the highly active components, namely $H_2O_2$ and the epoxide product.

Another major difficulty generally affecting epoxidation reactions involves temperature control in the epoxidation reactor. It is known that considerable heat is generated during epoxide formation. This heat must be rapidly dissipated from the reaction mixture in order to avoid the harmful consequences accompanying an excessive temperature increase. Since it is desired to avoid excessive agitation of the reaction mixture which would otherwise tend to improve heat transfer, this problem generally imposes serious process limitations. For example, in the case of an externally cooled column reactor, because of the low thermal conductivity of the oil phase, the column diameter must be limited in order to avoid an excessively high radial temperature gradient cf. H. K. Latourette et al., *J. Am. Oil Chem. s.:* 37 (1960).

DESCRIPTION OF THE INVENTION

Figure 1:
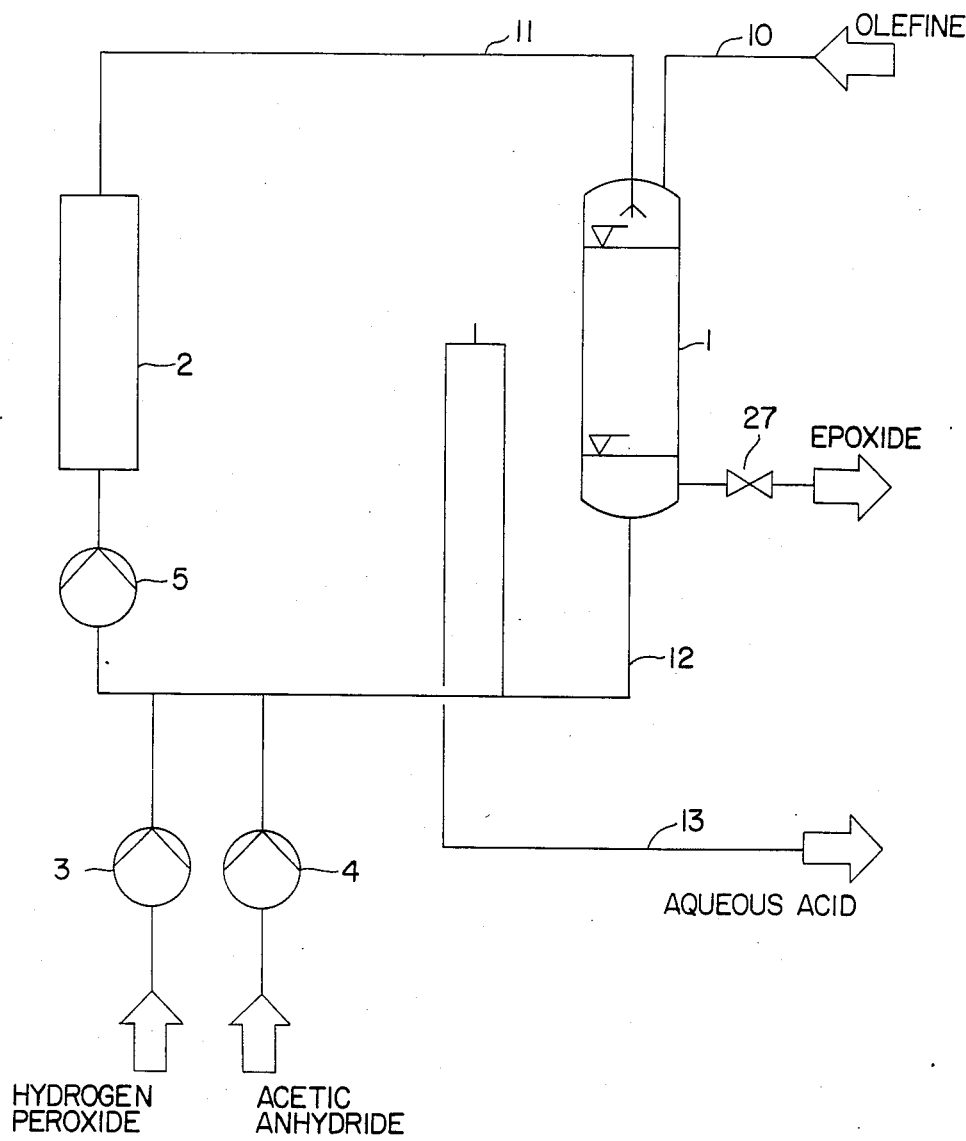
FIG. 1 illustrates a preferred arrangement for the batchwise epoxidation of an unsaturated hydrocarbon compound in relatively small quantities such as might be required when epoxidizing an olefin.

It is an object of the present invention to provide an improved process for the epoxidation of olefinically unsaturated hydrocarbon compounds. It is another object of the present invention to provide an epoxidation process that is applicable to olefinically unsaturated hydrocarbon compounds of varying quality.

These and other objects are achieved by the present invention wherein an aqueous acid phase is circulated between an epoxidation reactor and an acid regeneration stage. In the acid regeneration stage, the peracetic acid content of the aqueous acid phase discharged from the epoxidation reactor is increased and the "regenerated" aqueous acid phase is returned to the epoxidation reactor. By recirculating the aqueous acid phase in this fashion peracetic acid needed for epoxidation can be formed separate from the epoxidation reactor. As a result, peracetic acid can be used to epoxidize olefinically unsaturated hydrocarbon starting materials, which, hitherto, had been difficult to epoxidize.

Furthermore, the recirculating aqueous acid phase eases considerably the problem of temperature control in the epoxidation reactor by "internal cooling", while at the same time enabling peracetic acid to be formed in the circulating aqueous acid phase at a temperature optimal both for regeneration and for the prolonged use of the heterogeneous, solid acidic ion exchange resin regeneration catalyst.

The present invention particularly relates to a process for the epoxidation of olefinically unsaturated hydrocarbon compounds which are liquid at a temperature within the range of about 50° to 100° C. under normal (atmospheric) pressure. Any of the wide variety of normally liquid, unsaturated hydrocarbon compounds epoxidized in the prior art can be used in the present process. Suitable hydrocarbon compounds for epoxidation using the process of this invention are, in particular, olefins containing more than 12 carbon atoms, having terminal and/or internal sites of unsaturation such as 1-dodecene, 1-heptadecene, 1-hexadecene, 1-octadecene and 9-octadecene; unsaturated alcohols containing at least 8 carbon atoms, preferably fatty alcohols containing from 8 to 24 carbon atoms and more particularly 8 to 18 carbon atoms such as 10-hendecen-1-ol and olelyl alcohol; unsaturated carboxylic (fatty) acids containing at least 8 carbon atoms, preferably unsaturated fatty acids containing 8 to 24 carbon atoms and more particularly 8 to 18 carbon atoms, such as 10-hendecenoic acid, hexadecenoic acid, and oleic acid and esters of these unsaturated fatty acids with monohydric alcohols (methyl, ethyl, propyl, butyl, etc.) and/or polyhydric alcohols (glycols, glycerols, polyglycerols). A particularly useful class of starting materials is the fatty acid triglycerides.

In the present invention, starting materials of natural origin (e.g., fatty acids from animal or vegetable oils and fatty acid esters or fatty alcohols produced therefrom) containing a mixture of unsaturated and saturated hydrocarbon components need not be purified to remove the saturated constituents prior to epoxidation. In this connection, naturally occurring starting materials, in particular fatty acid triglycerides, for example of the soya oil type, may be used directly in the process of the present invention. The hydrocarbon starting material should be liquid at a temperature in the range at which the epoxidation reaction is conducted and will be referred to throughout the specification and claims as the "oil phase". The term "unsaturated hydrocarbon compound" or "hydrocarbon starting material" when used herein is to be understood to include compounds of the above type, e.g. olefins, unsaturated alcohols, and unsaturated carboxylic acids and esters thereof.

According to the present invention, the oil phase is contacted in an epoxidation reactor with an acid phase comprising acetic acid, hydrogen peroxide and peracetic acid in an aqueous solution. The aqueous acid phase is subsequently separated from the oil phase and the peracetic acid content in the aqueous acid phase is increased by regeneration over a suitable acidic ion exchange resin catalyst. Normally the aqueous acid phase is cooled before being delivered to the regeneration stage. The regenerated aqueous acid phase then is returned to the epoxidation reactor for further contacting.

The aqueous acid phase used in the present invention should contain at most about 10% by weight peracetic acid. Preferably, the aqueous acid phase fed to the epoxidation reactor has a peracetic acid content of only about 1 to 8% by weight and more preferably about 1.5 to 6% by weight. The water content of the aqueous acid phase preferably amounts to at least about 40% by weight and, more preferably, at least about 45% by weight. Normally, water comprises about 50% by weight or more of the aqueous acid phase. In the preferred embodiment, the hydrogen peroxide content of the aqueous acid phase does not exceed about 30% by weight, and may comprise for example, between about 15 and 30% by weight. The remainder of the aqueous acid phase comprises acetic acid. Thus, the acetic acid concentration typically is in the range of about 10 to about 20% by weight. A particularly preferred composition for the aqueous acid phase comprises approximately 15% by weight acetic acid, approximately 20 to 25% by weight hydrogen peroxide, approximately 1.5 to 5% by weight peracetic acid, and the remainder water.

In the epoxidation reactor, peracetic acid in the aqueous acid phase reacts with the olefinically unsaturated hydrocarbon compound (oil phase) to produce the epoxide product and acetic acid. As recognized by those skilled in this art, the epoxide products of the present invention can be used as plasticizers, as solvents and as reaction precursors for producing other commerically important products.

Epoxidation of the oil phase typically is conducted under known conditions of temperature and pressure. Epoxidation is preferably carried out at around normal (i.e., atmospheric) pressure and at a temperature above about 50° C., for example in the range of about 50°-80° C.

A temperature in the range of about 60° to 70° C. is particularly suitable for the epoxidation reaction.

The epoxidation stage can be operated in either a batchwise or a continuous fashion. When epoxidizing a relatively small quantity of an unsaturated reactant or, in cases where the unsaturated reactant to be epoxidized is changed relatively frequently, use of a batch epoxidation reactor may be preferred. Thus, a batch system may be preferred in the epoxidation of terminal and/or internal olefins containing more than 12 carbon atoms or in the production of epoxides of unsaturated fatty alcohols.

Referring to FIG. 1 an arrangement useful for epoxidizing an olefin in a batchwise manner is illustated. Epoxidation reactor 1 initially is filled with an unsaturated hydrocarbon compound such as an olefin via conduit 10. An acid stream comprising an aqueous mixture of hydrogen peroxide, acetic acid and peracetic acid then is introduced into reactor 1 through conduit 11 for contacting the oil phase. The acid stream flows through reactor 1; is separately recovered from the oil phase in conduit 12, and is deliverd by circulating pump 5 to regeneration stage 2. In regeneration stage 2, peracetic acid is formed by the catalytic reaction between hydrogen peroxide and acetic acid or acetic anhydride. Additional hydrogen peroxide and acetic acid or acetic anhydride are added to the recirculating acid in conduit 12 via pumps 3 and 4 respectively. A quantity of liquid necessary to balance the addition of new components to the acid stream is removed through conduit 13. The regenerated aqueous acid phase then is returned to reactor 1 through conduit 11. Once the oil phase has been completely epoxidized, the epoxide product is removed from reactor 1 through valved conduit 27.

Figure 2:
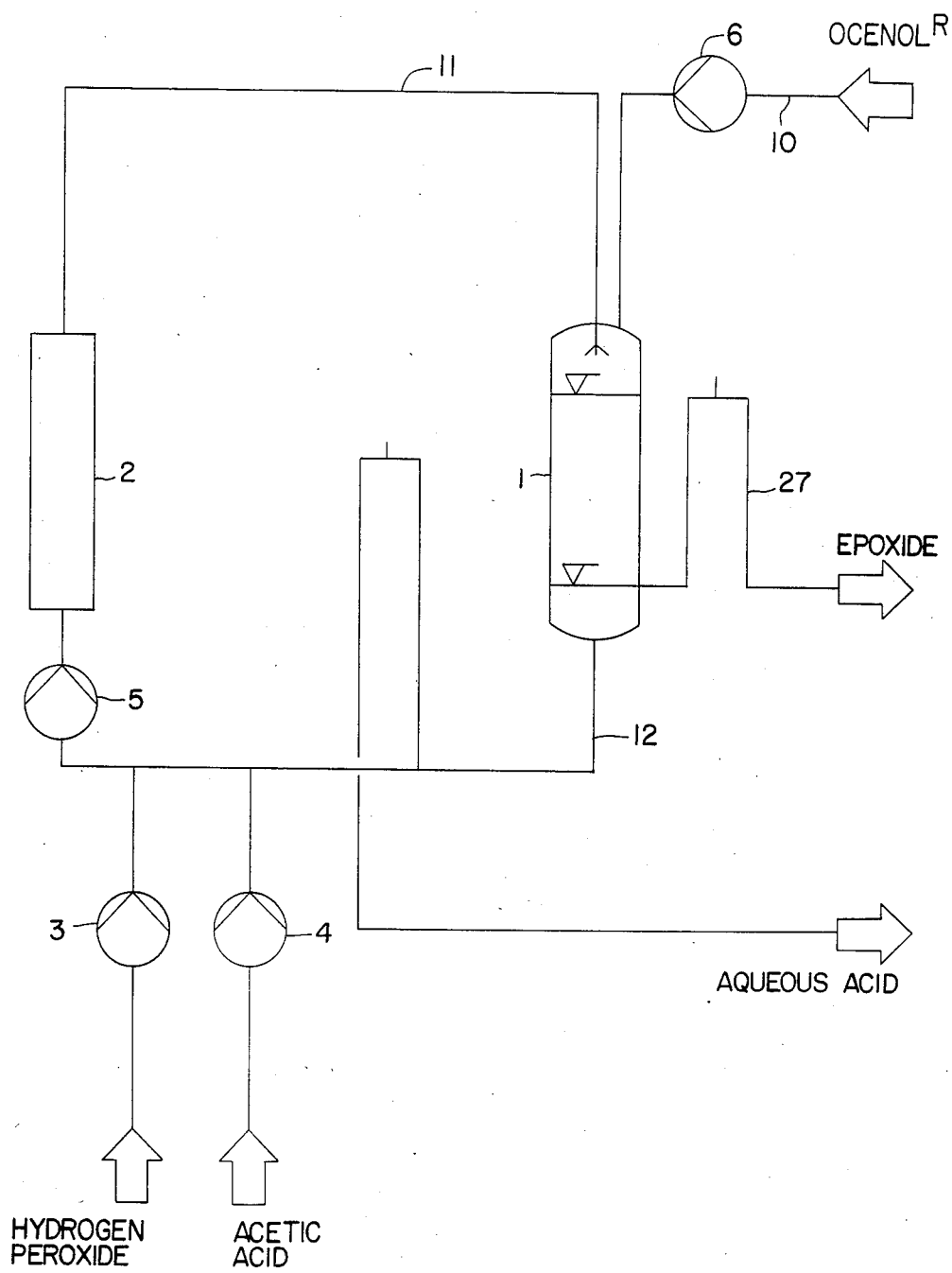
FIG. 2 illustrates an arrangement for epoxidizing an unsaturated hydrocarbon compound in a continuous fashion.

In order to conduct the expoxidation reaction continuously it is preferred to employ a packed reaction column through which the oil phase and the aqueous acid phase are flowed. A suitable arrangement is illustrated in FIG. 2. Preferably, the oil phase and the aqueous acid phase introduced through conduits 10 and 11 respectively are flowed concurrently in a downwards direction through the packed column reactor 1. The flow rate of the oil phase is controlled by feed pump 6. The oil phase forms the continuous phase in which the aqueous acid phase is dispersed. By suitably selecting the column packing, it is possible to adjust the degree of dispersity which both ensures a sufficiently fast reaction between the oil phase and the peracetic acid in the aqueous acid phase and, enables the aqueous acid phase to be readily separated from the oil phase at the base of the column reactor or after the reaction mixture has been recovered from the column reactor. For example, conditions are selected so that the droplets in the disperse aqueous acid phase are distinctly formed in the visible range (diameter from about 0.1 to 5 mm and preferably from about 0.5 to 3 mm).

The epoxide product is recovered in conduit 27 separately from the aqueous acid phase which is circulated via conduit 12 and pump 5 to the regeneration stage 2. The handling of the recirculating aqueous acid phase is identical to the FIG. 1 embodiment and thus requires no further description.

Preferably, the volumetric throughput of the aqueous phase in the epoxidation reactor is higher than than of the oil phase. Even where both streams of reactants flow co-currently downward through a column, as described above, differing flow rates are readily possible because the aqueous acid phase is the denser reactant, and descends through the oil phase. Thus, any desired flow ratio can be adjusted between the respective streams. When practicing the present invention, the ratio of the volumetric flow rate of the aqueous acid phase to the volumetric flow rate of the oil phase preferably is in the range of about 2:1 to about 50:1 and more preferably from about 20:1 to 40:1. In a conventional batch system, the volumetric flow rate of the aqueous acid phase is taken to be the product of the recirculation volume and the number of circuits completed by the circulating acid phase in the reaction time, while the volumetric flow rate of the oil phase is taken to be the volume of the epoxidation reactor. However, in a preferred continuous embodiment of the present invention, it is not only the aqueous acid phase which is circulated; but the oil phase also is circulated. In this case, the oil phase is returned to the epoxidation reactor after separation of the aqueous acid phase from the reaction mixture.

An important feature of the present invention is that because of the comparatively low concentration of the aqueous reactant in the epoxidation reactor only a limited quantity of the peracetic acid in the recirculating acid is consumed in the epoxidation reaction. In particular, the relative amounts of the oil phase and the aqueous acid phase in the epoxidation reactor are adjusted as noted above such that the contacting of the oil phase and the aqueous acid phase continues for a time period which causes the peracetic acid content of the aqueous acid phase to be reduced by at most about 50% as a result of the contacting. In fact, it may actually be advisable to operate with comparatively lower conversion levels. Thus, in a preferred embodiment of the present invention, the reaction in the epoxidation reactor is controlled in such a way that at most about 1.5% by weight of peracetic acid, based on the total weight of the aqueous acid phase, is reacted. It is particularly preferred to control the epoxidation reaction in such a way that only about 0.5 to 1% by weight of peracetic acid, again based on the total weight of the aqueous acid phase is consumed in one pass through the epoxidation reactor.

The combination of the relatively dilute peracetic acid concentration and specific droplet size of the aqueous phase in the reaction mixture ensures sufficiently rapid completion of the epoxidation reaction in the column. The dilute, aqueous acid phase not only functions as the oxidizing reactant, but it also serves as an internal coolant by taking up and dissipating considerable amounts of the heat of the exothermic epoxidation reaction. The comparatively low concentration of peracetic acid in the aqueous acid phase and the limited degree of reaction during a single passage of the acid phase through the reaction column are further factors which stabilize and control the epoxidation reaction.

According to the present invention, the aqueous acid phase is separately recovered from the epoxidation reactor and regeneration of the peracetic acid content in the aqueous acid phase is carried out by contacting a stream of the acid phase containing hydrogen peroxide with a suitable acidic cation exchange resin. Known, strongly acidic cation exchange resins, such as those used in the prior art can be used as the catalyst.

Preferred regeneration catalysts for use in the present invention are acidic cation exchange resins containing sulfonic acid groups. In addition to the commercial cation exchange resins previously mentioned, the ion exchange resins commercially available under the trademark "Lewatit SC 108" and "Lewatit SPC 108" (Bayer AG), "Amberlite MR 200" (Rohm & Haas) and "Permutit RSP 120" and Permutit RS-120" (Duolite International) also can be used.

The catalyst may take the form of a fixed bed through which the recirculating aqueous acid phase is flowed together with the additional hydrogen peroxide. If hydrogen peroxide is used as an aqueous concentrate, as is generally preferred, for example 70% wt. % hydrogen peroxide, it normally is advisable to co-introduce additional acetic acid and/or acetic acid anhydride while at the same time remove an equivalent quantity of liquid from the recirculating acid phase. Alternatively, the recirculating acid phase recovered from the epoxidation stage could be partly freed of water, before adding fresh hydrogen peroxide.

The initial concentration of hydrogen peroxide, acetic acid and water in the aqueous acid phase are important for obtaining the desired equilibrium concentration of peracetic acid in the aqueous acid phase afer catalytic regeneration in the acidic ion exchange resin bed. Reaction of hydrogen peroxide with acetic acid to form peracetic acid and water increases the amount of water in the aqueous acid phase. This increase in water content can be reduced if acetic acid anhydribe is used instead of acetic acid in the regeneration step. If regeneration is carried out by adding additional acetic acid or acetic acid anhydride into the recirculating acid phase, a corresponding amount of liquid must be removed, either batchwise or continuously, from the aqueous acid phase circuit. As will be recognized by those skilled in this art, provided that only water accumulating during formation of the peracetic acid is removed from the recirculating acid phase and provided that there are no losses of acetic acid or acetic acid anhydride in the epoxide product by virtue of their solubility in the oil phase, there is no need to add acetic acid or acetic acid anhydride to the recirculating aqueous acid phase.

The process of the present invention is not limited to only co-current epoxidation in a column but also may be conducted, for example, in stirrer-equipped autoclaves and in other known column reactor designs and the like. If desired, the epoxidation stage may even be divided into multiple sections or into multiple reactors arranged one after the other. Thus, soya oil for example may be continuously epoxidized with hydrogen peroxide and acetic acid in accordance with the present invention using the cross-countercurrent process described in German Appln. No. 33 20 219.2, providing each phase separator for recovering the aqueous acid phase of each epoxidation reactor is followed by a catalyst bed containing the acidic ion exchange resin for regenerating peracetic acid. This cross-countercurrent arrangement is illustrated in FIG. 3.

Figure 3:
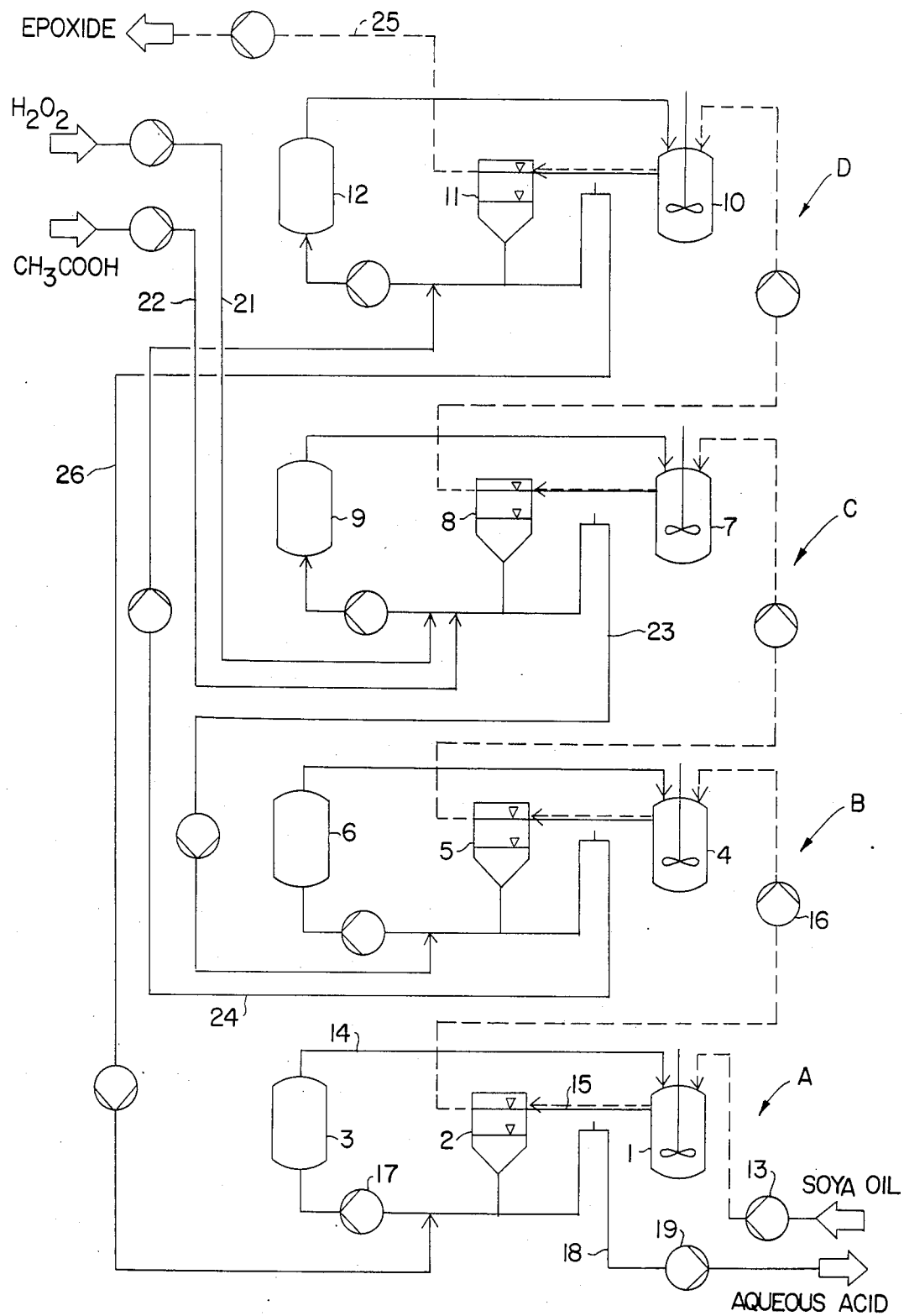
FIG. 3 illustrates a multiple staged, cross-countercurrent process for epoxidizing unsaturated hydrocarbon compounds.

As shown, the FIG. 3 arrangement consists of four treatment stages, A through D, with each stage having an epoxidation reactor, a phase separator and a regenerator. In this embodiment, reactors 1, 4, 7 and 10 simply comprise stirred tanks. The unsaturated hydrocarbon compound (oil phase) flows serially through the reactor and separator of each stage starting with reactor 1 (stage A) and separator 2 and proceeding through reactor-separator pairs 4 and 5 (stage B), 7 and 8 (stage C) and 10 and 11 (stage D). Epoxide product is recovered in conduit 25 from stage D. The flow of the oil phase is shown by the broken line. Each stage has a recycle circuit for the aqueous acid phase and the acid phase also is transferred between the stages in the following manner: acid from stage C flows through conduit 23 to stage B, acid from stage B flows through conduit 24 to stage D, acid from stage D flows through conduit 26 to stage A and acid from stage A is discharged through conduit 18. Fresh hydrogen peroxide and acetic acid is fed to the third stage C via conduits 21 and 22 respectively.

The operation of stage A will now be described, operation of the other stages being substantially the same. The unsaturated hydrocarbon compound is flowed into reactor 1 by pump 13 and is reacted with the aqueous acid phase introduced into reactor 1 through conduit 14. The combined oil and aqueous phases are discharged from reactor 1 through conduit 15 and each phase is separately recovered from separator 2. The recovered oil phase is flowed by pump 16 to the next epoxidation reactor 4 in stage B, while one portion of the acid phase is recirculated by pump 17 to regeneration stage 3 and then back to reactor 1 while another portion is discharged through conduit 18 by pump 19.

Another important feature of the present invention is that the epoxidation and regeneration reactions can be conducted at different conditions. Thus, it is preferred, for example, to carry out regeneration of the acid phase at a lower temperature than is used for epoxidation of the oil phase. Therefore, the aqueous acid phase preferably is cooled after separation from the oil phase. For example, regeneration of the aqueous acid phase to form peracetic acid preferably is conducted at a temperature in the range of about 15° to 60° C. and more preferably at a temperature in the range of about 20 to 40° C. By controlling the regeneration temperature in this manner and by preventing the oil phase from fouling the resin catalyst, the ion exchange catalyst substantially retains its high activity for promoting the formation of peracetic acid from hydrogen peroxide and acetic acid for an extended time.

Prior to the present invention, epoxidation of unsaturated fatty alcohols was totally inadequate because of yield-reducing secondary reactions. Using the process of the present invention, it is possible, for the first time, to produce directly epoxidized fatty alcohols in yields of more than 80%. Whereas, for example, when epoxidizing the alpha-olefin 1-dodecene using formic acid and hydrogen peroxide, a multistage batch process was required to achieve yields of the epoxide of more than 80% (at least 1.7 moles of hydrogen peroxide/mole of double bond and 0.5 mole of formic acid/mole of double bond (DB) having to be used). The same yield may be accomplished in a single stage using the process of the present invention. Furthermore, in the process of the present invention, there is no need to use a solvent such as chloroform, even when epoxidizing olefins. Thus, purification steps needed in certain prior art procedures are eliminated.

The general applicability of the process of the present invention to unsaturated hydrocarbon compounds of diverse orgin, the flexibility of the process to be adapted to the use of a variety of reactors for carrying out the epoxidation reaction and the application of co-current or countercurrent processes are all illustrated in the following examples. These examples are presented to illustrate further the present invention and are not intended to limit its scope which is defined by the appended claims.

Example 1 describes the non-continuous (batchwise) epoxidation of 1-dodecene. Example 2 describes the continuous epoxidation of an unsaturated fatty alcohol or fatty alcohol mixture having a carbon chain length of $C_{16}$ to $C_{18}$ and an iodine number of 88.3 in a packed column. Finally, Example 3 describes the continuous epoxidation of soya oil by the modified cross-countercurrent process according to the above-mentioned German patent application.

EXAMPLES

EXAMPLE 1

The alpha-olefin 1-dodecene (iodine number 150), was non-continuously epoxidized with hydrogen peroxide and acetic acid using the apparatus schematically illustrated in FIG. 1. First, 850 g of 1-dodecene were introduced into reactor 1 and the acid circuit was filled with an aqueous mixture of 22% by weight hydrogen peroxide, 25% by weight acetic acid, 5% by weight peracetic acid and 48% by weight water. The acid phase circulation pump 5 then was activated. The volumetric rate of circulation of the acid phase was 5 l/h. 366 g of a 70% by weight hydrogen peroxide aqueous concentrate (1.5 moles $H_2O_2$/mole DB) and 102 g of acetic acid anhydride (0.2 mole acetic acid anhydride/mole DB) then were successively pumped into the acid water circuit by pumps 3 and 4, respectively, while at the same time a corresponding amount of the recirculating aqueous acid phase was removed from the circuit. In regeneration stage 2, the circulating aqueous acid phase flowed through a fixed ion exchange resin bed consisting of 1 kg "Amberlite IR 118/M" manufactured by Rohm & Haas. The temperature in the regeneration stage was kept constant at 60° C. by indirect cooling.

After 10 hours, pump 5 was switched off, thus terminating the reaction. Epoxide product in reactor 1 was recovered and a new batch of 1-dodecene was introduced into the reactor. This batch then was epoxidized in the same way as described above. After termination of the reaction, an aqueous acid phase concentration was obtained which, ignoring minor fluctuations, corresponded to the above-described composition of the acid phase initially introduced with the first batch.

The epoxide produced in this way had an epoxide value of 7.2 (yield 83.8%) and an iodine number of 5.1 (conversion 96.6%).

EXAMPLE 2

An unsaturated $C_{16}-C_{18}$ fatty alcohol having an iodine number of 88.9 was continuously epoxidized with hydrogen peroxide and acetic acid using apparatus schematically shown in FIG. 2.

One hundred and thirty grams per hour of the fatty alcohol was continuously pumped by pump 6 into reactor 1. Reactor 1 had a useful volume of 1 l. Five liters per hour of an aqueous acid phase were circulated through regenerator 2 containing an ion exchange resin and through reactor 1 by pump 5. The formation of peracetic acid in regenerator 2 was balanced by the consumption of peracetic acid in reactor 1. 33.2 g/h (1.5 moles $H_2O_2$/mole DB) of 70% hydrogen peroxide and 13.7 g/h (0.5 mole acetic acid/mole DB) of acetic acid were continuously introduced into the recirculating aqueous acid phase. The liquid level and phase boundary in reactor 1 were adjusted by means of vented overflows. Regenerator 2 was filled with 1 kg of "Lewatiut SC 108" type ion exchange resin manufactured by Bayer AG.

The temperature in reactor 1 was kept constant at about 60° C. by indirect cooling (double jacket). To ensure uniform distribution of the aqueous acid phase over the cross-section of the reactor, the reactor was filled with glass Raschig rings.

The epoxide thus obtained had an epoxide value of 4.2 (yield 79.7%) and a residual iodine number of 4.5 (conversion 94.9%).

EXAMPLE 3

Using the apparatus schematically illustrated in FIG. 3, soya oil was epoxidized with acetic acid and hydrogen peroxide by the cross-countercurrent process described in German Appln. No. 33 20 219.2 using an ion exchange catalyst to accelerate the formation of the peracid. The plant comprised four stages, each stage consisting of a stirred-reactor, a phase separator and a fixed ion exchange resin bed (regenerator). The stirred-reactor and the phase separator each had a useful volume of 1 l; the fixed ion exchange resin bed contained 500 g of "Lewatit SC 108" ion exchange resin. In each stage, 1 liter of an aqueous acid phase was circulated through the ion exchange resin. In each reactor, the reaction temperature was kept at about 70° C. whereas the separator and the ion exchange beds were not temperature controlled.

Five hundred grams per hour of soya oil were continuously fed into reactor 1. The partially epoxidized soya oil then was passed through the separators and reactors in the sequence 2 - 4 - 5 - 7 - 8 - 10 - 11 (interrupted line). 149 g/h of 70% hydrogen peroxide (1.2 moles $H_2O_5$/mole DB) were continuously introduced into the aqueous acid phase circuit of the third stage consisting of reactor 7, separator 8 and fixed ion exchange bed 9. Apart from the aqueous acid phase recirculation in each stage, the acid water passed through the component units of the plant in the sequence 9 - 7 - 8 - 6 - 4 - 5 - 12 - 10 - 11 - 3 - 1 - 2.

A soya oil epoxide having an epoxide value of 6.6 and an iodine number of 4.8 was obtained.

Although certain embodiments of the invention have been described in detail, it will be appreciated that other embodiments are contemplated along with modification of the disclosed features, as being within the scope of the invention, which is defined in the appended claims.

We claim:

1. A process for the epoxidation of an olefinically unsaturated hydrocarbon compound which is liquid at a temperature within the range of about 50° to 100° C. and at atmospheric pressure comprising:
   (a) contacting said olefinically unsaturated hydrocarbon compound as an oil phase with an aqueous acid phase containing acetic acid, hydrogen peroxide and peracetic acid in aqueous solution, said aqueous acid phase containing at most about 10% by weight peracetic acid;
   (b) continuing said contacting for a period of time such that the peracetic acid content of the aqueous acid phase is reduced by at most about 50 wt. %, based on the peracetic acid content of the aqueous acid phase used;
   (c) separately recovering the aqueous acid phase from the oil phase;
   (d) regenerating the peracetic acid content of the separately recovered aqueous acid phase; and
   (e) recycling the regenerated aqueous acid phase for contacting said olefinically unsaturated hydrocarbon compound in step (a).

2. The process of claim 1, wherein the peracetic acid content of the aqueous acid phase is regenerated by adding hydrogen peroxide to said separately recovered aqueous acid phase and contacting said aqueous acid phase with an acidic cation exchange resin, said exchange resin containing a strongly acidic group.

3. The process of claim 2 wherein said strongly acidic group is a sulfonic acid group.

4. The process of claim 1 wherein said aqueous acid phase contains from about 1 to 8% by weight peracetic acid.

5. The process of claim 4 wherein said aqueous acid phase contains from about 1.5 to 6% by weight peracetic acid.

6. The process of claim 4 wherein the aqueous acid phase further contains at least about 30% by weight water and less than about 30% by weight hydrogen peroxide.

7. The process of claim 1 wherein the aqueous acid phase contains approximately 15% by weight acetic acid, approximately 20 to 25% by weight hydrogen peroxide, and approximately 1.5 to 5% by weight peracetic acid.

8. The process of claim 7 wherein the contacting of step (a) is continued for a time period such that the peracetic acid content of the aqueous acid phase is reduced by at most about 1.5% by weight based on the weight of the aqueous acid phase.

9. The process of claim 8 wherein the peracetic acid content of the aqueous acid phase is reduced by at most about 0.5 to 1% by weight based on the weight of the aqueous acid phase.

10. The process of claim 1 wherein said separately recovered aqueous acid phase is cooled prior to regenerating the peracetic acid content in step (d).

11. The process of claim 10 wherein the contacting of step (a) is carried out at atmospheric pressure and at a temperature in the range of about 50° to 80° C. and, the regeneration of step (d) is carried out at temperatures in the range of about 15° to 60° C.

12. The process of claim 11 wherein said contacting is carried out at a temperature in the range of about 60° to 70° C.

13. The process of claim 12 wherein said regeneration is carried out at a temperature in the range of about 20° to 40° C.

14. The process of claim 1 wherein the flow ratio of aqueous acid phase to oil phase in the contacting of step (a) is preferably within the range of about 2:1 to 50:1.

15. The process of claim 14 wherein said flow ratio is in the range of about 20:1 to 40:1.

16. The process of claim 1 wherein the contacting of step (a) is carried out in a packed column through which the oil phase and the aqueous acid phase flow co-currently downwardly.

17. The process of claim 1 wherein said olefinically unsaturated hydrocarbon compound is selected from the group consisting of olefins containing more than 12 carbon atoms, unsaturated alcohols containing at least 8 carbon atoms, unsaturated fatty acids containing at least 8 carbon atoms; and the esters of said unsaturated fatty acids with monohydric or polyhydric alcohols.

18. The process of claim 17 wherein said unsaturated alcohol comprises a fatty alcohol containing 8 to 18 carbon atoms.

19. The process of claim 17 wherein said unsaturated fatty acid contains from 8 to 18 carbon atoms.

20. The process of claim 17 wherein said fatty acid ester comprises a triglyceride.

21. The process of claim 20 wherein said triglyceride comprises soya oil.

* * * * *